US010745656B2

(12) United States Patent
Compo et al.

(10) Patent No.: US 10,745,656 B2
(45) Date of Patent: Aug. 18, 2020

(54) METHOD OF FORMING AND USING DEACTIVATION WIPE KIT

(71) Applicant: Veltek Associates, Inc., Malvern, PA (US)

(72) Inventors: Mark J. Compo, Doylestown, PA (US); Michael Balestri, Mechanicsville, VA (US)

(73) Assignee: VELTEK ASSOCIATES, INC., Malvern, PA (US)

( * ) Notice: Subject to any disclaimer, the term of this patent is extended or adjusted under 35 U.S.C. 154(b) by 127 days.

(21) Appl. No.: 16/175,530

(22) Filed: Oct. 30, 2018

(65) Prior Publication Data

US 2019/0062678 A1  Feb. 28, 2019

Related U.S. Application Data

(63) Continuation of application No. 15/271,957, filed on Sep. 21, 2016, now Pat. No. 10,138,448.

(60) Provisional application No. 62/320,999, filed on Apr. 11, 2016.

(51) Int. Cl.

| | |
|---|---|
| *C11D 17/04* | (2006.01) |
| *B65D 30/24* | (2006.01) |
| *B65D 81/22* | (2006.01) |
| *B65D 75/58* | (2006.01) |
| *A61L 2/18* | (2006.01) |
| *B65B 5/04* | (2006.01) |
| *B65B 7/02* | (2006.01) |
| *B65B 51/10* | (2006.01) |
| *B65B 55/08* | (2006.01) |
| *A61L 2/08* | (2006.01) |
| *B65B 55/02* | (2006.01) |

(52) U.S. Cl.
CPC .............. *C11D 17/049* (2013.01); *A61L 2/18* (2013.01); *B65B 5/045* (2013.01); *B65B 7/02* (2013.01); *B65B 51/10* (2013.01); *B65B 55/08* (2013.01); *B65D 31/14* (2013.01); *B65D 31/145* (2013.01); *B65D 75/5805* (2013.01); *B65D 81/22* (2013.01); *A61L 2/08* (2013.01); *A61L 2202/17* (2013.01); *B65B 55/027* (2013.01); *B65B 2210/06* (2013.01)

(58) Field of Classification Search
CPC ......... C11D 17/04; C11D 17/049; A61L 2/18; A61L 2/08; A61L 2202/17; B65B 5/045; B65B 7/02; B65B 1/10; B65B 55/08; B65B 55/027; B65B 2210/06; B65B 31/14; B65B 31/145; B65B 75/5805; B65B 81/22

USPC ......................................................... 588/320
See application file for complete search history.

(56) References Cited

U.S. PATENT DOCUMENTS

| | | |
|---|---|---|
| 3,625,351 A | 12/1971 | Eisenberg |
| 3,930,041 A | 12/1975 | Komatsu et al. |
| 5,811,113 A | 9/1998 | Dorr et al. |
| 6,387,384 B1 | 5/2002 | Probert et al. |
| 7,066,354 B2 | 6/2006 | Stank et al. |
| 8,080,216 B2 | 12/2011 | Green et al. |
| 8,162,137 B2 | 4/2012 | Vellutato, Jr. et al. |
| 9,108,208 B2 | 8/2015 | Vellutato, Jr. et al. |
| 2005/0221113 A1 | 10/2005 | Bitowft et al. |
| 2009/0238502 A1 | 9/2009 | Bhattacharjee et al. |
| 2011/0084098 A1 | 4/2011 | Py |
| 2012/0269459 A1 | 10/2012 | Howes |
| 2013/0095058 A1 | 4/2013 | Bylemans et al. |
| 2014/0033655 A1 | 2/2014 | Stanley et al. |
| 2014/0034081 A1 | 2/2014 | Asano |
| 2014/0143857 A1 | 5/2014 | Maim |
| 2014/0215969 A1 | 8/2014 | Parthun et al. |
| 2015/0101287 A1 | 4/2015 | Vellutato, Jr. |
| 2015/0125502 A1 | 5/2015 | Colurciello et al. |
| 2015/0336788 A1 | 11/2015 | Vellutato, Jr. et al. |

FOREIGN PATENT DOCUMENTS

FR        2876358 A1    4/2006

OTHER PUBLICATIONS

European Search Report for EP Application No. EP 17782818, dated Oct. 30, 2019, 8 pages.
Hypo-Chlor® 5.25% Wipe, Safety Data Sheet, Veltek Associates, Inc., vol. 77, No. 58, Mar. 26, 2012, 6 pages.
ExpressWeb EFS 174, Product Definition Sheet, Glenroy, Inc., Nov. 3, 2010, 10 pages.
WipeDown 1-2-3, Wipe Kit, Mar. 23, 2016, [retrieved from the internet on May 23, 2017] URL: https://www.linkedin.com/pulse/finally-sterile-wiper-kit-usp800-compliance-jason-willett>; p. 1.
International Search Report and Written Opinion issue din PCT/US17/23760 dated Jun. 15, 2017.

*Primary Examiner* — Edward M Johnson
(74) *Attorney, Agent, or Firm* — Blank Rome LLP

(57) ABSTRACT

A hazardous drug deactivation wipe kit includes a first pouch having a one-way valve coupled to an end thereof, a second pouch, and a third pouch. The first pouch contains a wipe saturated in a hypochlorite solution, the second pouch contains a wipe saturated in thiosulfate solution, and the third pouch contains a wipe saturated in isopropyl alcohol solution. The deactivation wipe kit may be used in a clean room to deactivate most hazardous drugs on a work surface.

13 Claims, 3 Drawing Sheets

METHOD OF FORMING AND USING DEACTIVATION WIPE KIT

RELATED APPLICATIONS

The present application claims the benefit of U.S. Provisional Application No. 62/320,999, filed Apr. 11, 2016, whose disclosure is hereby incorporated by reference in its entirety into the present disclosure.

FIELD OF THE INVENTION

The invention relates to a wipe kit used for deactivation, decontamination, and disinfection or cleaning in a clean room environment and a method of preparing and using the same.

BACKGROUND OF THE INVENTION

A clean environment or controlled environment is a space designed, maintained, and controlled to prevent particle and microbiological contamination of products. Clean environments include clean rooms and clean workspaces (such as hooded workspaces), which are collectively referred to here as a clean room. Clean rooms are most commonly designed for use in manufacturing facilities and medical research and treatment facilities in the pharmaceutical, biotechnology, and healthcare industries, to name a few. Sterile clean room environments may be classified under a variety of classification schemes, including the International Organization of Standardization ("ISO") Cleanroom Standards, whereby the highest level of sterilization is an ISO 1 clean room and a normal ambient air environment (no sterilization) is classified as ISO 9.

Certain chemical compositions are used inside clean rooms including, for instance, germicidal disinfectants such as phenols, cleaners, quaternary ammonium, peracetic acid, as well as various sporicides, such as peracetic acid, bleach, and hydrogen peroxide. The disinfectants and sporicides are used in clean rooms to disinfect clean room surfaces. In certain clean room environments, such as those in the healthcare industry, surfaces can become exposed to certain hazardous drugs. In those situations, chemicals are needed that can deactivate and decontaminate hazardous drugs on work surfaces to reduce the risk of occupational exposure to technicians and other workers in the clean room, as well as to products or chemicals being prepared in the clean room. The methods of deactivating, decontaminating and disinfecting/cleaning surfaces exposed to hazardous drugs must meet the requirements set forth in USP <800> and USP <797> set forth by the U.S. Pharmacopeial Convention (USP). Conventional methods of clean room sterilization are lacking for this purpose because they do not adequately deactivate the hazardous drugs, but instead simply spread the drug around on the affected surface. On the other hand, products that may be capable of deactivating hazardous drugs are not suitable for use inside of a classified ISO 5 clean room.

Further, the chemical compositions, which are not naturally sterile, need to be sterilized before being able to enter the clean room to avoid risk of contamination. Such compositions can be sterilized by filtration inside of the clean room or can be sterilized before entering the clean room.

To sterilize the compositions outside the clean room, the concentrated composition is either terminally sterilized by irradiation or aseptically processed. To terminally irradiation sterilize the composition, the composition is placed in a container, double bagged, and placed in a lined carton. The entire carton is then terminally sterilized by irradiation. A procedure for terminally irradiation sterilizing a composition is described, for instance, in U.S. Pat. No. 6,123,900 to Vellutato, the disclosure of which is incorporated herein by reference. Some chemicals used in a clean room, however, cannot be irradiated because of their chemical makeup and structure. For example, certain chemicals used to deactivate and decontaminate hazardous drugs in clean rooms cannot be irradiated. This creates problems for introducing such chemicals into a clean room environment and complicates the sterilization process.

Accordingly, the invention is directed to a deactivation wipe kit that improves deactivation, decontamination, and disinfection/cleaning of hazardous drugs from sterile surfaces in a clean room. The deactivation wipe kit of the invention is also able to be irradiated outside of the clean room environment for more efficient transfer and introduction into a clean room.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
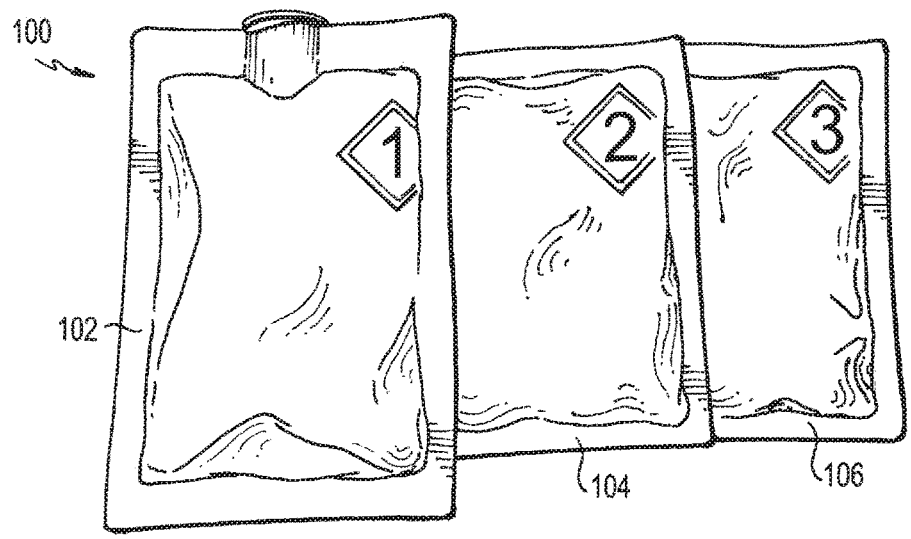
FIG. 1 is a front, perspective view of the deactivation wipe kit according to an embodiment of the invention.

Referring now to FIG. 1, a deactivation wipe kit 100 is illustrated. As used more fully herein, the term "wipe kit" is used to refer to the deactivation wipe kit 100. In one embodiment, the wipe kit 100 includes three pouches 102, 104, 106. Each of these pouches contains a wipe that is saturated in a different chemical used to deactivate and decontaminate hazardous drugs in a clean room environment and disinfect the work surface. In use, the technician applies each wipe from each of the pouches 102, 104, 106 in sequence to a contaminated work surface, such that the wipe in the first pouch 102 is used first, the wipe in the second pouch 104 is used second, and the wipe in the third pouch 106 is used last. When used in this way, the deactivation wipe kit 100 deactivates, decontaminates, and disinfects/cleans most hazardous drugs from work environments for compounding sterile preparations, such as an ISO 5 clean room, as cited by USP <800> and USP <797> set forth by the U.S. Pharmacopeial Convention (USP).

In one embodiment, the first pouch 102 contains a wipe that is saturated in a 5.25% hypochlorite solution, such as sodium hypochlorite (e.g., HYPO-CHLOR® available commercially from Veltek Associates, Inc. of Malvern, Pa.). This composition is the primary agent that deactivates the hazardous drug(s). It deactivates potentially active drugs that may be present on a compounding surface, and renders the surface safe and decontaminated for future handlers and ensures that the compounding preparations are following USP <797> compounding sterile preparations for patient protection protocol along with USP <800> compliance for hazardous drugs (handling in healthcare settings). While the use of sodium hypochlorite is preferred, any chemical known to deactivate hazardous drugs may be used to saturate the wipe in the first pouch 102, including, but not limited to, potassium permanganate and alkaline potassium permanganate.

The second pouch 104 contains a wipe that is saturated in 2% thiosulfate, such as sodium thiosulfate (e.g., THIO-WIPE™ available commercially from Veltek Associates, Inc). In a preferred embodiment, the thiosultate is USP Grade. This composition is used in order to remove the hypochlorite solution residue from the treated work surface. The thiosulfate renders the hypochlorite, which is a corrosive material, neutral on the surface so as to maintain the surface's structure and integrity. It also functions to decontaminate the work surface. While sodium thiosulfate is preferred, any chemical known to decontaminate a work surface that has been treated with hypochlorite, and which can neutralize the same, may be used. Thus, the sodium thiosulfate solution cleans, decontaminates, and neutralizes the sodium hypochlorite solution and previously deactivated hazardous drugs. It improves the overall longevity of the sterile compounding equipment and stays USP <797> and USP <800> compliant.

The third pouch 106 contains a wipe that is saturated in 70% isopropyl alcohol (IPA) (e.g., ALCOH-WIPE® available commercially from Veltek Associates, Inc.), which functions as a disinfectant. In a preferred embodiment, the IPA is USP Grade. This wipe further cleans and disinfects the treated surface and returns the surface back to its original condition for worker safety. While IPA is preferred, any chemical known to clean and disinfect a work surface may be used, including, but not limited to, sterile water or known germicidal agents such as phenols, quats, peroxyacetic acid (POAA) and $H_2O_2$. Thus, the IPA provides an additional measure against contaminates present on the compounding surfaces for added protection. After deactivation of the work surface, additional disinfection is needed to maintain a critical, controlled, work environment for compounding sterile products.

All three chemicals used in each of the pouches 102, 104, 106 may be formulated with Water for Injection (WFI) and filtered at 0.2 microns. Once a surface is fully treated by all three wipes, the surface can return to its natural composition.

Each of the wipes contained in pouches 102, 104, 106 is preferably formed of a non-woven, non-shedding material that is designed to be clean, have good absorption properties, and provide good surface coverage. The wipe should have good non-shedding properties, as fibers from the wipe should not be easily detached from the wipe so as to avoid contaminating the clean room work surface. In one embodiment, the wipe of the first pouch 102 is formed of 100% polypropylene, while the wipes in the second pouch 104 and third pouch 106 are formed of 100% polyester. In this embodiment, the material of each wipe is chosen for its compatibility with the particular chemical present in each of the pouches 102, 104, 106. Each of these materials produces a fabric-like wipe that is strong, has good non-shedding particulate performance, and is compatible with the chemical in which it is saturated as well as use in a controlled environment. In one embodiment, the wipe is about 9"×12" in size such that it can treat a surface area of approximately six (6) square feet.

In one embodiment, the wipe for the first pouch 102 is a 162XL-4019, 48 gauge polyester with an ALOX coating bonded to 150 (6 mil) white polytheylene. This particular substrate retains the active hypochlorite, though other suitable wipes can be provided. Further, this wipe material minimizes the degradation and instability associated with hypochlorite caused by exposure to organic material. In one embodiment, a single wipe is provided in each pouch 102, 104, 106; however more than one wipe can be provided in any or all of the pouches 102, 104, 106.

Figure 2:
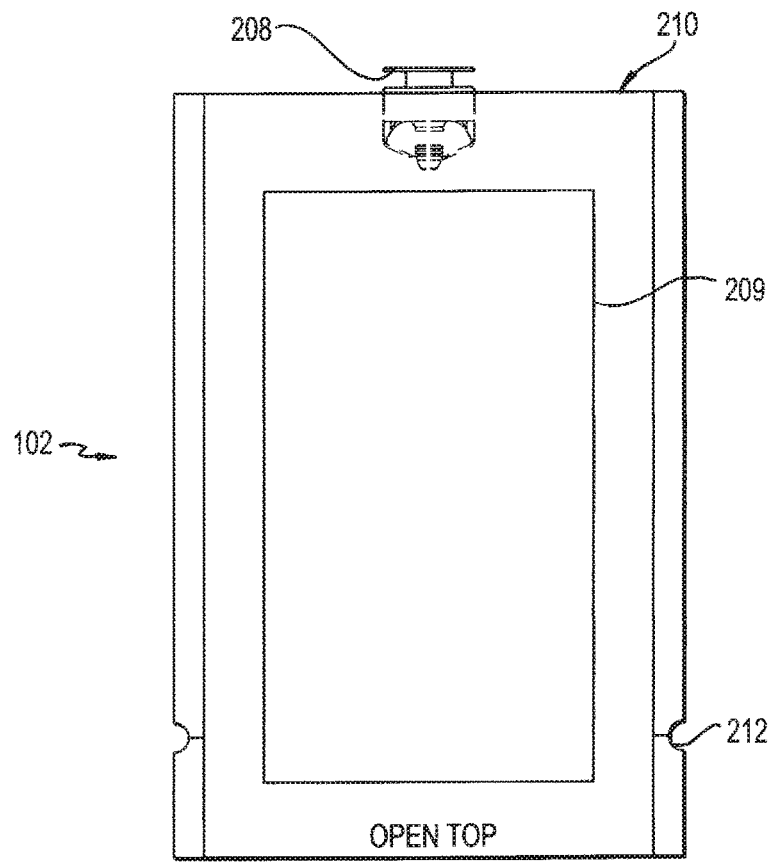
FIG. 2 is a front, plan view of the first pouch of the deactivation wipe kit having a one-way valve according to an embodiment of the invention.
Figure 3A:
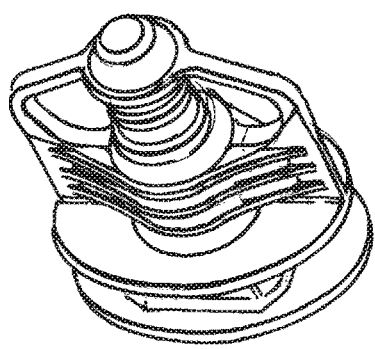
FIGS. 3A-E are perspective views of the one-way valve illustrated in FIG. 2.
Figure 3B:
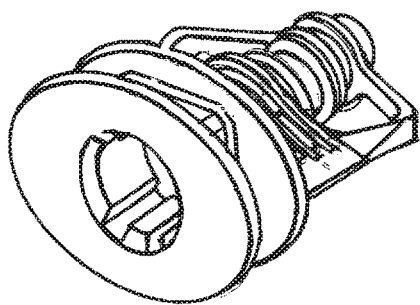
Figure 3C:
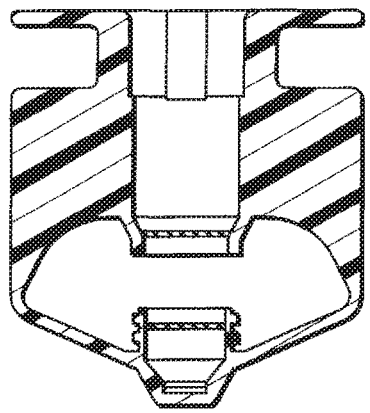
Figure 3D:
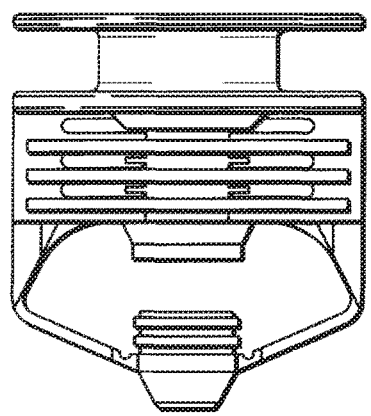
Figure 3E:
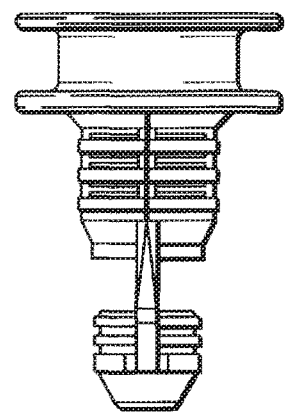

The pouches 102, 104, 106 themselves are designed as flexible packaging structures for the wipes. The pouches 102, 104, 106 are preferably formed of a material that provides a barrier to moisture, air and light and has good chemical resistance so as to maintain its structural integrity during irradiation and when ultimately shelved in the clean room. In one embodiment, each pouch 102, 104, 106 is formed of a multi-layered structure comprised of layers of coated polyester, low density polyethylene, aluminum foil, hydroxypropylcellulose, and/or linear low density polyethylene. For example, the pouches 102, 104, 106 can be ExpressWeb EFS174, by by Glenroy Inc., which is attached hereto and hereby incorporated by reference. When prepared into a multi-layered structure, these materials provide an air-tight and liquid-tight seal and are highly chemically resistant (since stability of the finished product can be affected by light, oxygen and organic matter). They also help to maintain the active agents in each of the chemicals so as to prolong their shelf life. Each of the pouches 102, 104, 106 preferably includes a notch or perforation 212, such as shown in FIG. 2 in the first pouch 102. The notch 212 can be formed in the side of the pouch 102, 104, 106, so that the user can tear open the pouch 102, 104, 106 by pulling on the side of the pouch at the notch 212. Thus in use, the technician pulls the pouch along the perforation in order to tear the pouch 102, 104, 106 open to access the saturated wipe contained therein.

In order to introduce the deactivation wipe kit 100 into the clean room, it (and its contents) must first be sterilized. In one embodiment, parts of the deactivation wipe kit 100 is irradiated to avoid introducing contaminants into the environment. The second pouch 104 and third pouch 106 contain chemicals that may be terminally irradiation sterilized, such as by the methods described herein. Thus, assembled pouches 104, 106 may undergo known terminally irradiation sterilization. The first pouch 102, however, contains a chemical (i.e., sodium hypochlorite) that cannot be terminally irradiation sterilized. As such, the first pouch 102 is configured differently than the second pouch 104 and third pouch 106 such that the chemical can be added after the first pouch 102 has been sterilized.

As set forth in FIG. 2, the first pouch 102 is designed with a one-way valve 208 positioned at an end 210 thereof, and the pouch 102 contains a wipe 209. This valve 208, which is more fully illustrated in FIGS. 3A-E, only allows fluids to be transferred through it in one direction. As such, the first pouch 102, containing only a dry wipe, may be terminally irradiation sterilized, together with the second pouch 104 and third pouch 106 (each of which contain the wipe and the respective chemical). Then, when the pouches 102, 104, 106 are transferred to the clean room, the first pouch 102 may be aseptically filled with the sterilized hypochlorite solution via the one-way valve 208 to saturate the dry wipe contained therein. The sterilized hypochlorite solution may be of any concentration determined suitable to one or ordinary skill in the art. For example, a hypochlorite concentration of 5.25% is used. At this point, the deactivation wipe kit 100 is fully ready for use in a clean room. The wipes contemplated for the kit may be of any conventional size known in the art, exemplarily 3"×4", 4"×6", 9"×9", 9"×12", or 12"×12".

Figure 4:
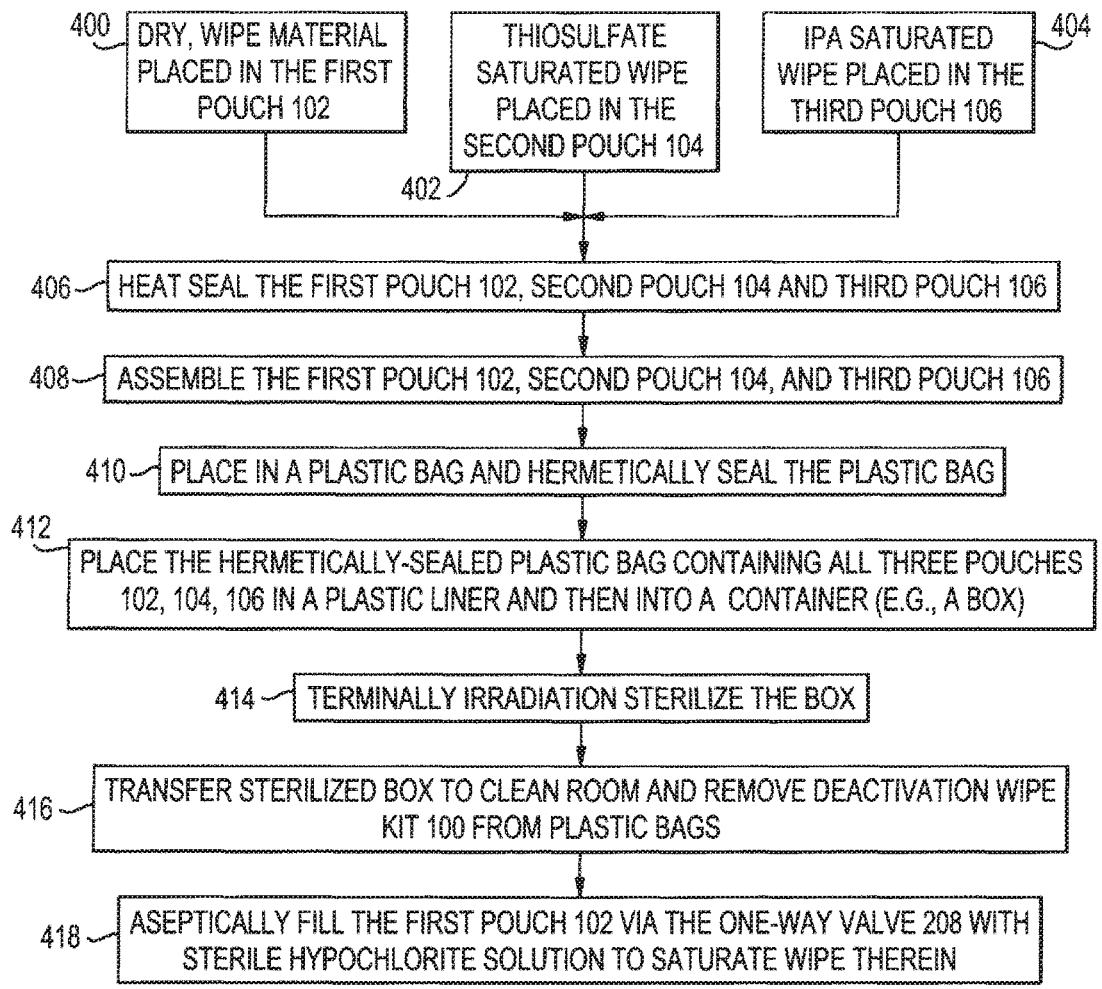
FIG. 4 is a flowchart outlining the steps of a method of preparing a deactivation wipe kit according to an embodiment of the invention.

A process of preparing the deactivation wipe kit 100 is outlined in the flow chart of FIG. 4. Each pouch 102, 104, 106 may be prepared in sequence or simultaneously by different technicians. Thus, Steps 400, 402, 404 can be performed sequentially or at the same time. As set forth more fully below, each of the steps utilizes the chemicals and materials described above.

In Step 400, a dry, wipe material is placed in the first pouch 102 and hermetically sealed to form a first closed or sealed container or pouch. At this step, there are no chemicals present in the first pouch 102. A wipe saturated with a first solution, such as for example thiosulfate solution (e.g., THIO-WIPE®), is placed in the second pouch 104 and hermetically sealed to form a second closed or sealed container or pouch, Step 402. A wipe saturated with a second solution, such as for example 70% IPA (by concentration) (e.g., ALCOH-WIPE®), is placed in the third pouch 106 and hermetically sealed to form a third closed or sealed container or pouch, Step 404. Each of the pouches 102, 104, 106 is hermetically sealed, Step 406, to enclose the contents of each pouch. In one embodiment, the hermetic seal is a liquid and air tight seal of the pouches 102, 104, 106, such as for example a heat seal. Though the heat sealing, Step 406, is shown as a separate step, it can be part of each of the filling processes of Steps 400, 402, 404.

Each of the first, second and third sealed pouches 102, 104, 106 are assembled in preparation for irradiation sterilization, Step 408. One of each of the first, second, and third sealed pouches 102, 104, 106 are assembled together and placed in a first container such as a first plastic bag and the first plastic bag is then hermetically sealed to form a first closed or sealed pouch enclosure, Step 410. Optionally, the first sealed pouch enclosure can be placed in a second container such as a second plastic bag and the second plastic bag is then hermetically sealed to form a second closed or sealed pouch enclosure. In one embodiment, the first and second plastic bags are a polyethylene bag that is heat sealed. The second (or first) sealed pouch enclosure is then placed into a plastic liner bag (e.g., a polyethylene bag) which is closed and placed into a box or other container. The liner is then closed (such as by being knotted or by a fastener (tie)) and the box is closed to form a closed package, Step 412. The box and the enclosed contents are then terminally irradiation sterilized using known techniques and equipment, Step 414, and can be shipped to an irradiator for sterilization, to form a sterilized closed container. The irradiation sterilizes the container and its contents, including the plastic bags, wipes, pouches, solutions.

The irradiated boxes (sterilized closed containers) are then transferred to a clean environment and the sterilized closed pouch enclosure is removed from the plastic liner bag. The sterilized first, second and third sealed pouches are then removed from the inner-most sealed plastic bag, Step 416. At this point, the second sealed pouch 104 and the third sealed pouch 106 are ready for use. However, the first sealed pouch 102 must be filled with the deactivation chemical. In one embodiment, the first sealed pouch 102 is aseptically filled with a sterile hypochlorite solution via the one-way valve 208 inside the clean room, Step 418. At this step, when the first pouch 102 is filled with the solution, the solution is allowed to saturate the dry wipe in the pouch 102, thereby preparing a saturated, hypochlorite wipe. The valve 208 may close automatically by virtue of its design, though other suitable valve designs can be provided.

Once the valve 208 is closed, the first sealed pouch 102 forms a first closed or sealed filled pouch that is then ready for use as well. Optionally, the first sealed filled pouch 102 can be successively hermetically sealed in a first container and optionally then a second container, such as plastic bags to form a first (and second) first filled pouch enclosure. Once the first sealed filled pouch 102 (or first/second filled pouch enclosure) is ready for use, it is matched with one of the irradiated second sealed pouch 104 and one of the irradiated third sealed pouch 106, to form the deactivation wipe kit 100. Optionally, the deactivation wipe kits 100 can be successively hermetically heat sealed in a first container (e.g., a polyethylene bag) and optionally then a second container (e.g., a polyethylene bag), such as plastic bags. Multiple wipe kits 100 are then placed together into a carton having a plastic liner. The plastic liner can be closed (such as by being knotted or by a fastener (tie)) and the box is closed to form the final closed package. The box can then be shipped to the customer for use.

Alternate processes of preparing the deactivation wipe kit 100 may also be performed. The drying, wiping, and placement of material in the first pouch 102 (Step 400) may be performed before, during, or after the placement of the thiosulfate-saturated wipe in the second pouch 104 (Step 402), and before, during or after the IPA-saturated wipe is placed in the third pouch 106 (Step 404). Similarly, the placement of the thiosulfate-saturated wipe in the second pouch 104 (Step 402) and the placement of the IPA-saturated wipe in the third pouch 106 (Step 404) may occur in any order relative to the preparation of the other pouches, as long as all three pouches 102, 104, and 106 can be prepared prior to the step of heat sealing, if packaged together in a same box. However, the irradiated second and third pouches can be packaged together in a box separate from the first final pouch.

In addition it will further be appreciated that other suitable techniques can be utilized to irradiation sterilize the pouches 102, 104, 106. For instance, the multiple pouches 102, 104, and/or 106 can be heat sealed in the same or different individual first (and optionally second) plastic bags. In one embodiment, each closed pouch 102, 104, 106 can be individually single/double bagged (i.e., heat sealed in a first plastic bag (and optionally a successive second plastic bag) to form respective first and second sealed enclosures for the first, second and third closed pouches), then placed in a carton liner and a box and sterilized. In another embodiment, multiple first closed pouches 102 can be heat sealed together in a first bag to form a first enclosure, multiple second closed pouches 104 can be heat sealed in a second bag to form a second enclosure, and multiple third closed pouches 106 can be heat sealed in a third bag to form a third enclosure; and the first, second and third enclosures can be placed in a liner and box and simultaneously irradiated.

Still further, multiple first closed pouches 102 can individually be single/double bagged and placed into a first box; multiple second closed pouches 104 can individually be single/double bagged and placed into a second box; and multiple third pouches 106 can individually be single/double bagged and placed into a third box. Or, multiple first sealed pouch enclosures can be placed in a first box for irradiation, and multiple second and third pouch enclosures can be placed together in a second box for irradiation. In addition, the first and second containers can be any suitable containers such as pouches, and the first, second and third pouches 102, 104, 106 can be any suitable container.

Figure 5:
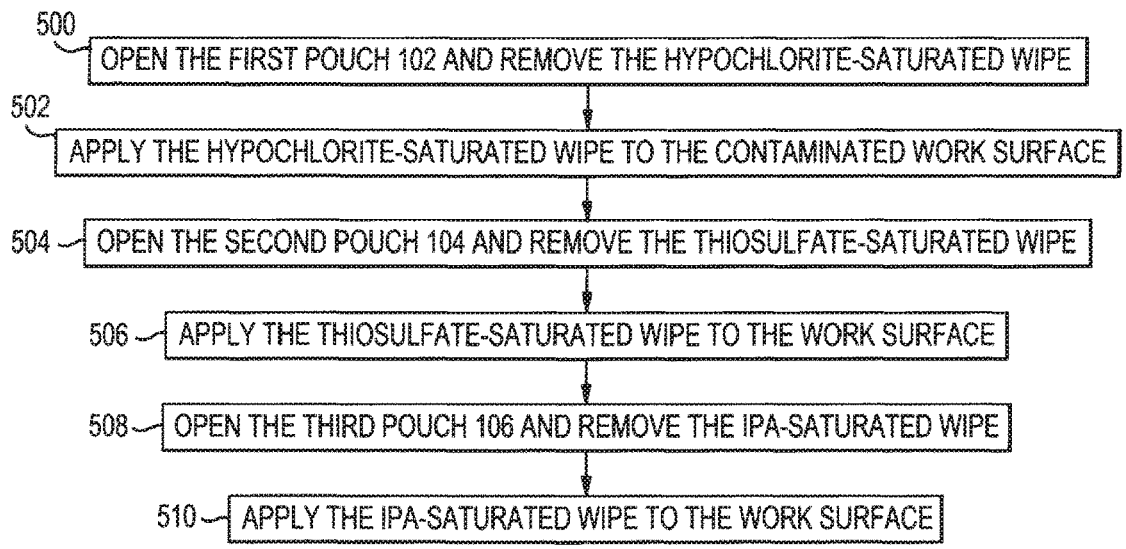
FIG. 5 is a flowchart outlining the steps of a method of using the deactivation wipe kit according to an embodiment of the invention.

Thus, an end user can receive a single box having multiple kits, each kit having a first, second and third sterilized closed pouch. A method of using the deactivation wipe kit 100 is outlined in FIG. 5. Once the box arrives at the customer, the box and box liner are opened (e.g., in a clean room or staging area). A kit 100 can then be removed from the box for use, and brought into the clean room. The heat sealed bag is opened and the pouches 102, 104, 106 are removed. As set forth in Step 500, the first pouch 102 is opened (e.g., by tearing the perforation 212) and the hypochlorite-saturated wipe is removed. The wipe is then applied to the contaminated work surface in order to deactivate the hazardous drug(s), Step 502. Next, the second pouch 104 is opened and the thiosulfate-saturated wipe is removed, Step 504. The wipe is then applied to the work surface that has just be treated with the hypochlorite-saturated wipe, Step 506, in order to decontaminate the surface and remove any hypochlorite residue that may still be present on the surface. The third pouch 106 is then opened and the IPA-saturated wipe is removed, Step 508. Lastly, the wipe is applied to the work surface in order to disinfect and clean the surface to render it safe for use by a technician or worker, Step 510. Once each wipe is used consecutively on the surface, any hazardous drugs that are present are deactivated and decontaminated and the surface is disinfected and safe for use by the technician.

Thus, multiple variations of the invention are apparent within the scope of the present invention. The first, second and third pouches can be individually single/double-bagged (i.e., hermetically sealed in a first pouch and successive second pouch). Or the second and third pouches can be single/double-bagged together for irradiation and delivery to the end user; and either matched in a box with a double-bagged first filled pouch enclosure or boxed separately from the single/double-bagged first filled pouch enclosure. Still other variations are possible within the spirit and scope of the invention. For instance, the end user can receive a first box with the first sterilized closed pouches, and a second box with the second and third sterilized closed pouches. In addition, although the invention is described for use with three pouches each having a different solution, other suitable number of pouches and solutions can be provided, such as two or four or more.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended Claims.

What is claimed:

1. A method of preparing a deactivation wipe kit, comprising the steps of:
   (a) placing a dry wipe in a first pouch having a one-way valve coupled to an end thereof;
   (b) placing a thiosulfate-saturated wipe in a second pouch;
   (c) placing an isopropyl alcohol-saturated wipe in a third pouch;
   (d) hermetically sealing the first pouch, the second pouch, and the third pouch to respectively form a first closed pouch, second closed pouch and third closed pouch;
   (e) placing the first closed pouch, the second closed pouch, and the third closed pouch in a plastic bag and hermetically sealing the plastic bag to form a closed pouch enclosure;
   (f) placing the closed pouch enclosure in a container and irradiation sterilizing the container and its contents to form a sterilized closed container;
   (g) transferring the sterilized closed container to a controlled environment and removing the first closed pouch, the second closed pouch, and third closed pouch from the closed pouch enclosure;
   (h) aseptically filling the first closed pouch with sterile hypochlorite solution via the one-way valve to saturate the dry wipe with hypochlorite solution.

2. The method of preparing a deactivation wipe kit according to claim 1, wherein step (d) and/or step (e) are performed by heat sealing the first pouch, the second pouch, the third pouch and/or the plastic bag.

3. The method of preparing a deactivation wipe kit according to claim 1, wherein steps (a)-(c) may be formed sequentially or simultaneously.

4. The method of preparing a deactivation wipe kit according to claim 1, wherein the step (e) further comprising placing the first closed pouch, the second closed pouch, and the third closed pouch in a first plastic bag and hermetically sealing the first plastic bag to form a first closed pouch enclosure, and placing the first closed pouch enclosure in a second plastic bag to form a second closed pouch enclosure.

5. The method of preparing a deactivation wipe kit according claim 1, wherein step (h) forms a first closed filled pouch, and further comprising the step of placing the first closed filled pouch, the second closed pouch and the third closed pouch in a final plastic bag and hermetically sealing the final plastic bag to form a final closed pouch enclosure.

6. The method of preparing a deactivation wipe kit according to claim 5, further comprising the step of placing the final closed pouch enclosure in a liner and a container.

7. The method of preparing a deactivation wipe kit according to claim 1, wherein said step of irradiation sterilizing sterilizes the first pouch, second pouch, third pouch, dry wipe, thiosulfate-saturated wipe, isopropyl alcohol-saturated wipe, plastic bag, and container.

8. A method of using a deactivation wipe kit comprised of a first pouch having a one-way valve coupled to an end thereof, the first pouch containing a wipe saturated in hypochlorite solution;
   a second pouch containing a wipe saturated in thiosulfate solution; and
   a third pouch containing a wipe saturated in isopropyl alcohol solution,
   wherein the deactivation wipe kit may be used in a clean room to deactivate hazardous drugs on a work surface;
   wherein the method of use comprises the steps of:
   (a) removing the wipe from the first pouch and applying the wipe to a work surface contaminated with at least one hazardous drug;
   (b) removing the wipe from the second pouch and applying the wipe to the work surface;
   (c) removing the wipe from the third pouch and applying the wipe to the work surface,
   wherein step (a) deactivates the hazardous drug, step (b) decontaminates the work surface, and step (c) disinfects and cleans the work surface.

9. The method of claim 8, wherein steps (a)-(c) are performed in sequential order.

10. The method of claim 8, wherein each of the wipes are removed from the first pouch, the second pouch, and the third pouch, respectively, by tearing a perforation in each of the first pouch, the second pouch, and the third pouch.

11. A method of preparing a wipe kit, comprising the steps of:
(a) placing a dry first wipe in a first pouch having a one-way filling valve coupled to an end thereof and closing the first pouch to form a first closed pouch;
(b) placing a second wipe saturated with a second solution in a second pouch and closing the second pouch to form a second closed pouch;
(c) irradiation sterilizing the first closed pouch to form a first sterilized closed pouch;
(d) irradiation sterilizing the second closed pouch to form a second sterilized closed pouch; and
(e) filling the first sterilized closed pouch with a first solution via the one-way filing valve to saturate the dry first wipe with the first solution.

12. The method of claim 11, wherein the step (e) forms a first sterilized filled closed pouch, and further comprising the step of placing the first sterilized filled closed pouch in a first bag and hermetically sealing the first bag to form a first sterilized filled closed pouch enclosure.

13. The method of claim 11, further comprising the step of placing the second closed pouch in a second bag and hermetically sealing the second bag to form a second closed pouch enclosure.

* * * * *